(12) United States Patent
Hesse et al.

(10) Patent No.: US 9,587,006 B2
(45) Date of Patent: Mar. 7, 2017

(54) IGF-I POLY (ETHYLENE GLYCOL) CONJUGATES

(75) Inventors: Friederike Hesse, Munich (DE); Eva Hoess, Neuried (DE); Stephanie Mueller, Eppelheim (DE); Eva Maria Trost-Gross, Wolfratshausen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 13/577,284

(22) PCT Filed: Feb. 4, 2011

(86) PCT No.: PCT/EP2011/051631
§ 371 (c)(1),
(2), (4) Date: Aug. 6, 2012

(87) PCT Pub. No.: WO2011/098400
PCT Pub. Date: Aug. 18, 2011

(65) Prior Publication Data
US 2012/0309679 A1    Dec. 6, 2012

(30) Foreign Application Priority Data
Feb. 11, 2010   (EP) .................................. 10153275

(51) Int. Cl.
| | | |
|---|---|---|
| C07K 14/65 | (2006.01) |
| A61K 47/48 | (2006.01) |
| C07K 5/11 | (2006.01) |
| C12P 21/06 | (2006.01) |
| C07K 1/107 | (2006.01) |

(52) U.S. Cl.
CPC ........ *C07K 14/65* (2013.01); *A61K 47/48215* (2013.01); *C07K 1/1075* (2013.01); *C07K 5/1019* (2013.01); *C12P 21/06* (2013.01)

(58) Field of Classification Search
CPC .... C07K 5/1019; C07K 1/1075; C07K 14/65; A61K 47/48215
See application file for complete search history.

(56) References Cited

U.S. PATENT DOCUMENTS

| | | | |
|---|---|---|---|
| 5,932,462 A | 8/1999 | Harris et al. | |
| 6,303,337 B1 * | 10/2001 | Rothschild et al. | 435/69.1 |
| 7,459,526 B2 | 12/2008 | Bordusa et al. | |
| 2006/0024679 A1 * | 2/2006 | Voges et al. | 435/6 |
| 2006/0154865 A1 | 7/2006 | Amrein et al. | |
| 2008/0064079 A1 | 3/2008 | Hoess et al. | |

FOREIGN PATENT DOCUMENTS

| | | |
|---|---|---|
| EP | 0490249 | 6/1992 |
| EP | 0473084 | 11/1995 |
| GB | EP 1767545 * | 3/2007 |
| JP | 2009207449 | 9/2009 |
| WO | 94/01451 | 1/1994 |
| WO | 94/12219 | 6/1994 |
| WO | 95/32003 | 11/1995 |
| WO | WO 95/32003 * | 11/1995 |
| WO | 00/44785 | 8/2000 |
| WO | 2006/015879 | 2/2006 |
| WO | 2006066891 | 6/2006 |
| WO | 2007/036299 | 4/2007 |
| WO | 2008/025528 | 3/2008 |

OTHER PUBLICATIONS

Heiger, 1993, Peptide Mapping and Analysis Using Capillary Electrophoresis, Hewlett Packard, Application Note, pp. 1-6.*
Veronese, Biomaterials 22:405-417 (2001).
Davey et al., Intl Journal of Peptide & Protein Research 45(4):380-385 (Apr. 1995).
Sato, Advanced Drug Delivery Reviews 54:487-504 (2002).
Brown, Expert Opinion Drug Deliv. 2(1):29-42 (2005).
Lewinska et al., Bioconjugate Chemistry 15(2):231-234 (2004).
Pasut et al., Expert Opin. Ther. Patents 14(6):859-894 (2004).
Veronese et al., Drug Discovery Today 10(21):1451-1458 (2005).
Ausubel et al. Current Protocols in Molecular Biology (Table of Contents only),John Wiley & Sons, Inc., vol. 1-3:Table of Contents (2001).
Kozlowski et al., Journal of Controlled Release 72:217-224 (2001).
Terpe, Appl. Microbiol. Biotechnol. 60:523-533 (2003).
Schellenberger et al., Angew. Chem. Int. Ed. Engl. 30:1437-1449 (1991).
Wood et al., Infection and Immunity 59(5):1818-1822 (May 1991).
Delgado et al., Critical Reviews in Therapeutic Drug Carrier Systems 9(3,4):249-304 (1992).
Lu et al., Reactive Polymers 22:221-229 (1994).
Francis et al., International Journal of Hematology 68:1-18 (1998).
Sambrook et al. Molecular Cloning A Laboratory Manual (Cover and Table of Contents only), 2 edition,Cold Spring Harbor Laboratory,:Table of Contents (1989).
Mao et al., Journal American Chemical Society 126:2670-2671 (2004).
(Intl Search Report for PCT/EP2011/051631 Feb. 4, 2011).
The Japanese Office Action, issued on Feb. 18, 2014, in the corresponding Japanese application No. 2012-552344.

* cited by examiner

*Primary Examiner* — Prema Mertz
(74) *Attorney, Agent, or Firm* — Jones Day

(57) ABSTRACT

Herein is reported a method for producing of a polypeptide conjugated to one poly (ethylene glycol) comprising a) providing a nucleic acid encoding an expression construct comprising in 5' to 3' direction a nucleic acid encoding a polypeptide, and a nucleic acid encoding a trypsin site of SEQ ID NO: 01, b) expressing the nucleic acid of a) in a cell and recovering the expression construct from the cell and/or the cultivation medium, c) providing a target peptide with an amino acid sequence of SEQ ID NO: 02 covalently conjugated to a poly (ethylene glycol) at the C-terminal lysine residue, d) incubating the expression construct and the target peptide with the trypsin mutant D189K, K60E, N143H, E151H, and e) recovering and thereby producing the polypeptide conjugated to one poly (ethylene glycol) from the incubation mixture.

3 Claims, 4 Drawing Sheets

Fig. 1

| His Tag | Spacer | IgA-Protease Cleavage | IGF-1 WT | Trypsin-Site | Strep-Tag |

| His Tag | Spacer | IgA-Protease Cleavage | IGF-1 WT | Trypsin-Site |

| His Tag | Spacer | IgA-Protease Cleavage | IGF-1 (K27R, K65R) | Trypsin-Site |

SEQUENCE LISTING

<160> NUMBER OF SEQ ID NOS: 30

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      modified trypsine site peptide

<400> SEQUENCE: 1

Tyr Arg His Ala Ala Gly
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      target peptide

<400> SEQUENCE: 2

Arg His Ala Lys
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      displaced part of the tryp site peptide

<400> SEQUENCE: 3

Arg His Ala Ala Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      remaining peptide

<400> SEQUENCE: 4

Tyr Arg His Ala Lys
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      IgA protease cleavage site 1 peptide

<400> SEQUENCE: 5

Pro Ala Pro Ser Pro
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic IgA protease cleavage site 2 peptide

<400> SEQUENCE: 6

Pro Pro Ser Pro
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      IgA protease cleavage site 3 peptide

<400> SEQUENCE: 7

Pro Pro Ala Pro
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      IgA protease cleavage site 4 peptide

<400> SEQUENCE: 8

Pro Pro Thr Pro
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      IgA protease cleavage site 5 peptide

<400> SEQUENCE: 9

Pro Pro Gly Pro
1

<210> SEQ ID NO 10
<211> LENGTH: 103
<212> TYPE: PRT
<213> ORGANISM: Artificial Sequence
<220> FEATURE:
<223> OTHER INFORMATION: Description of Artificial Sequence: Synthetic
      IGF-I polypeptide 1

<400> SEQUENCE: 10

Met His His His His His His Arg Ala Arg Arg Phe Arg Arg His Pro
1               5                   10                  15

Arg Pro Pro Gly Pro Glu Thr Leu Cys Gly Ala Glu Leu Val Asp Ala
            20                  25                  30

Leu Gln Phe Val Cys Gly Asp Arg Gly Phe Tyr Phe Asn Lys Pro Thr
        35                  40                  45

Gly Tyr Gly Ser Ser Arg Arg Ala Pro Gln Thr Gly Ile Val Asp
    50                  55                  60

Glu Cys Cys Phe Arg Ser Cys Asp Leu Arg Leu Glu Met Tyr Cys
65                  70                  75                  80

Ala Pro Leu Lys Pro Ala Lys Ser Ala Tyr Arg His Ala Ala Gly Trp
                85                  90                  95

Ser His Pro Gln Phe Glu Lys

-continued

```
                100

<210> SEQ ID NO 11
<211> LENGTH: 95
<212> TYPE: PRT
<213> ORGANISM: Artificial Sequence
<220> FEATURE:
<223> OTHER INFORMATION: Description of Artificial Sequence: Synthetic
      IGF-I polypeptide 2

<400> SEQUENCE: 11

Met His His His His His His Arg Ala Arg Arg Phe Arg Arg His Pro
1               5                   10                  15

Arg Pro Pro Gly Pro Glu Thr Leu Cys Gly Ala Glu Leu Val Asp Ala
            20                  25                  30

Leu Gln Phe Val Cys Gly Asp Arg Gly Phe Tyr Phe Asn Lys Pro Thr
        35                  40                  45

Gly Tyr Gly Ser Ser Ser Arg Arg Ala Pro Gln Thr Gly Ile Val Asp
    50                  55                  60

Glu Cys Cys Phe Arg Ser Cys Asp Leu Arg Arg Leu Glu Met Tyr Cys
65                  70                  75                  80

Ala Pro Leu Lys Pro Ala Lys Ser Ala Tyr Arg His Ala Ala Gly
                85                  90                  95

<210> SEQ ID NO 12
<211> LENGTH: 95
<212> TYPE: PRT
<213> ORGANISM: Artificial Sequence
<220> FEATURE:
<223> OTHER INFORMATION: Description of Artificial Sequence: Synthetic
      IGF-I polypeptide 3

<400> SEQUENCE: 12

Met His His His His His His Arg Ala Arg Arg Phe Arg Arg His Pro
1               5                   10                  15

Arg Pro Pro Gly Pro Glu Thr Leu Cys Gly Ala Glu Leu Val Asp Ala
            20                  25                  30

Leu Gln Phe Val Cys Gly Asp Arg Gly Phe Tyr Phe Asn Arg Pro Thr
        35                  40                  45

Gly Tyr Gly Ser Ser Ser Arg Arg Ala Pro Gln Thr Gly Ile Val Asp
    50                  55                  60

Glu Cys Cys Phe Arg Ser Cys Asp Leu Arg Arg Leu Glu Met Tyr Cys
65                  70                  75                  80

Ala Pro Leu Arg Pro Ala Lys Ser Ala Tyr Arg His Ala Ala Gly
                85                  90                  95

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      Strep-tag peptide

<400> SEQUENCE: 13

Trp Ser His Pro Gln Phe Glu Lys
1               5

<210> SEQ ID NO 14
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      IgA protease cleavage site 6 peptide

<400> SEQUENCE: 14

Ala Pro Arg Pro
1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      IgA protease cleavage site 7 peptide

<400> SEQUENCE: 15

Pro Ala Pro Arg Pro
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      IgA protease cleavage site 8 peptide

<400> SEQUENCE: 16

Pro Ala Pro Gly Pro
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      IgA protease cleavage site 9 peptide

<400> SEQUENCE: 17

Pro Pro Thr Pro Ser Pro
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      IgA protease cleavage site 10 peptide

<400> SEQUENCE: 18

Pro Arg Pro Pro Thr Pro
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      IgA protease cleavage site 11 peptide

<400> SEQUENCE: 19

Pro Arg Pro Pro Ser Pro
1               5
```

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      IgA protease cleavage site 12 peptide

<400> SEQUENCE: 20

Pro Arg Pro Pro Ala Pro
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      IgA protease cleavage site 13 peptide

<400> SEQUENCE: 21

Pro Pro Arg Pro Pro Gly Pro
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      IgA protease cleavage site 14 peptide

<400> SEQUENCE: 22

Lys Pro Ala Pro Ser Pro
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      IgA protease cleavage site 15 peptide

<400> SEQUENCE: 23

Ser Thr Pro Pro Thr Pro
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      IgA protease cleavage site 16 peptide

<400> SEQUENCE: 24

Val Ala Pro Pro Ser Pro
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      IgA protease cleavage site 17 peptide

```
<400> SEQUENCE: 25

Ala Pro Arg Pro Pro Gly Pro
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      IgA protease cleavage site 18 peptide

<400> SEQUENCE: 26

Pro Ala Pro Arg Pro Pro Gly Pro
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      Strep-tag 1 peptide

<400> SEQUENCE: 27

Ala Trp Arg His Pro Gln Phe Gly Gly
1               5

<210> SEQ ID NO 28
<211> LENGTH: 94
<212> TYPE: PRT
<213> ORGANISM: Artificial Sequence
<220> FEATURE:
<223> OTHER INFORMATION: Description of Artificial Sequence: Synthetic
      mono-PEGylated human IGF-I polypeptide

<400> SEQUENCE: 28

Met His His His His His His Arg Ala Arg Arg Phe Arg Arg His Pro
1               5                   10                  15

Arg Pro Pro Gly Pro Glu Thr Leu Cys Gly Ala Glu Leu Val Asp Ala
            20                  25                  30

Leu Gln Phe Val Cys Gly Asp Arg Gly Phe Tyr Phe Asn Lys Pro Thr
        35                  40                  45

Gly Tyr Gly Ser Ser Ser Arg Arg Ala Pro Gln Thr Gly Ile Val Asp
    50                  55                  60

Glu Cys Cys Phe Arg Ser Cys Asp Leu Arg Arg Leu Glu Met Tyr Cys
65                  70                  75                  80

Ala Pro Leu Lys Pro Ala Lys Ser Ala Tyr Arg His Ala Lys
                85                  90

<210> SEQ ID NO 29
<211> LENGTH: 75
<212> TYPE: PRT
<213> ORGANISM: Artificial Sequence
<220> FEATURE:
<223> OTHER INFORMATION: Description of Artificial Sequence: Synthetic
      His-tag cleavaed mono-PEGylated IGF-I polypeptide

<400> SEQUENCE: 29

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30
```

```
Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala Tyr Arg His Ala Lys
65                  70                  75

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 30

His His His His His His
1               5
```

IGF-I POLY (ETHYLENE GLYCOL) CONJUGATES

RELATED APPLICATIONS

This application is the National Stage of International Application No. PCT/EP2011/051631, filed Feb. 4, 2011, which claims the benefit of European Application No. 10153275.2, filed Feb. 11, 2010, which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jun. 27, 2012, is named 26585. txt and is 10,741 bytes in size.

Herein is reported a method for the selective enzymatic C-terminal conjugation of a first polypeptide comprising a poly (ethylene glycol) residue to a second polypeptide, i.e. a method for enzymatic PEGylation.

BACKGROUND OF THE INVENTION

The importance of protein therapeutics has grown immensely over the past decades, as this class of drugs is targeting therebefore untreatable diseases. The formulation of protein drugs is challenging as their molecular size is very different from traditional low molecular weight substances. Furthermore, proteins have several other characteristics like their secondary and tertiary structure essential for proper functionality. They are susceptible to many types of degradation or modification and their formulation has to ensure stability and has to remain within their efficacious and safe target doses.

Other problems concerning proteins as pharmaceutical compounds are caused within the patient, e.g. immunogenic reactions, rapid clearance from the body leading to a reduced half-life, as well as proteolytic cleavage destructing the drug before performing its action (Brown, L. R., Expert Opinion Drug Deliv. 2 (2005) 29-42).

To address these problems one approach is to include chemical alterations in protein molecules, e.g. covalently attaching one or more poly (ethylene glycol) residues to the protein drug. This procedure is called PEGylation. The advantages of PEGylation are the increase in molecular weight and hydrodynamic size of the resulting conjugate. The new conjugate is less easy accessible for proteolytic enzymes as well as neutralizing antibodies or immune cells. As a result PEGylation is useful to prevent the drug from undesired cleavage and also decreases the possibility of allergic side-effects. The increased size is also influencing the clearance from the body, because the protein-PEG conjugate is too big to be removed by renal ultrafiltration (Veronese, F. M. and Pasut, G., Drug Discovery Today 10 (2005) 1451-1458; Brown, L. R., Expert Opinion Drug Deliv. 2 (2005) 29-42). Poly (ethylene glycol) itself improves the properties of the new drug immensely. In addition PEG's lack of toxicity is a major advantage. Taken together PEGylation is a well known method for increasing the blood circulation life time of a protein pharmaceutical (Kozlowski, A. and Harris, M. J., Journal of Controlled Release 72 (2001) 217-224). A variety of PEGylated protein drugs is commercially available, e.g. PEG-Intron® from Schering Plough, Somavert® from Pfizer and Pegasys® from Roche Pharmaceuticals (Pasut, G., et al., Expert Opinion on Therapeutic Patents 14 (2004) 859-894).

There is great interest for enzymatic site-specific modifications with mild conditions, high chemo- and regio-specifity and proper product yields. Several attempts in this field have been made. Mao et al. (Mao, H., et al., J. Am. Chem. Soc. 126 (2004) 2670-2671) developed a method of sortase-mediated protein ligation for C-terminal modification. Sato (Sato, H., Advanced Drug Delivery Reviews 54 (2002) 487-504) established a system using transglutaminase to introduce poly (ethylene glycol) site-specifically into intact and chimeric proteins inheriting a special substrate sequence for transglutaminase. Immunoglobulin A protease (IgA protease) has been used by Lewinska et al. (Lewinska, M., et al. Bioconjugate Chemistry 15 (2004) 231-234) to modify the N-terminus of native proteins. A mutated trypsin enzyme has been developed by Hoess et al. (WO 2006/015879).

SUMMARY OF THE INVENTION

Herein is reported a method for the selective C-terminal covalent conjugation of a polypeptide to one or more poly (ethylene glycol) molecule(s). This is a method, in which a small peptide covalently conjugated to poly (ethylene glycol) is enzymatically transferred to a polypeptide of interest to be PEGylated. It has been found that the presence of a Strep-tag C-terminal to the trypsin cleavage site enhances C-terminal site-specific modification.

A first aspect as reported herein is a method for producing of a polypeptide conjugated to a poly (ethylene glycol) residue comprising
  a) providing a nucleic acid encoding a fusion polypeptide comprising in 5' to 3' direction
     i) a nucleic acid encoding a polypeptide, and
     ii) a nucleic acid encoding an amino acid sequence of SEQ ID NO: 01,
  b) expressing the nucleic acid of a) in a cell and recovering the fusion polypeptide from the cell and/or the cultivation medium,
  c) providing a target peptide with an amino acid sequence of SEQ ID NO: 02 covalently conjugated to a poly (ethylene glycol) residue at the C-terminal lysine residue,
  d) incubating the fusion polypeptide and the target peptide with the trypsin mutant D189K, K60E, N143H, E151H, and
  e) recovering and thereby producing the polypeptide conjugated to one poly (ethylene glycol) residue from the incubation mixture.

In one embodiment the incubating comprises
  i) incubating the fusion polypeptide and the target peptide with guanidinium hydrochloride in a buffered solution,
  ii) incubating the trypsin mutant D189K, K60E, N143H, E151H with a Zn(II)-salt,
  iii) combining and incubating the incubation mixtures of i) and ii).

In one embodiment of the methods as reported herein the fusion polypeptide comprises in N- to C-terminal direction the polypeptide to be PEGylated, a trypsin-4x-mutant cleavage site and a Strep-tag. In another embodiment the nucleic acid encoding the fusion polypeptide comprises in 5' to 3' direction i) a nucleic acid encoding the polypeptide to be PEGylated, ii) a nucleic acid encoding an amino acid sequence of SEQ ID NO: 01, and iii) a nucleic acid encoding a Strep-tag of SEQ ID NO: 13 or 27.

In another embodiment the incubating is for a total of 150 minutes to 180 minutes. In a further embodiment the nucleic acid encoding the fusion polypeptide comprises in addition iii) a nucleic acid encoding an amino acid sequence of SEQ ID NO: 13. In one embodiment the polypeptide is human IGF-I.

In one embodiment the incubating is in HEPES buffered solution. In a further embodiment the incubating in the HEPES buffered solution is for at least 20 hours. In another embodiment the incubating is from 20 hours to 54 hours. In still another embodiment the incubating is at 20° C.

In one embodiment the fusion polypeptide has an amino acid sequence selected from SEQ ID NO: 10, SEQ ID NO: 11, or SEQ ID NO: 12. In a further embodiment the nucleic acid encoding a fusion polypeptide is a nucleic acid encoding a polypeptide with the amino acid sequence of SEQ ID NO: 10, or SEQ ID NO: 11, or SEQ ID NO: 12.

Also an aspect as reported herein is a polypeptide that has the amino acid sequence of SEQ ID NO: 28 or SEQ ID NO: 29 and that is conjugated to one poly (ethylene glycol) residue at the C-terminal lysine residue.

One aspect as reported herein is a pharmaceutical composition comprising a polypeptide that has the amino acid sequence of SEQ ID NO: 28 or SEQ ID NO: 29 and that is conjugated to one poly (ethylene glycol) residue at the C-terminal lysine residue or a polypeptide obtained with the method as reported herein.

A further aspect as reported herein is the use of a polypeptide that has the amino acid sequence of SEQ ID NO: 28 or SEQ ID NO: 29 and that is conjugated to one poly (ethylene glycol) residue at the C-terminal lysine residue or a polypeptide obtained with a method as reported herein for the manufacture of a medicament for the treatment of Alzheimer's disease.

Still as aspect as reported herein is a polypeptide that has the amino acid sequence of SEQ ID NO: 28 or SEQ ID NO: 29 and that is conjugated to one poly (ethylene glycol) residue at the C-terminal lysine residue or a polypeptide obtained with the method as reported herein for use as a medicament.

One aspect as reported herein is a polypeptide that has the amino acid sequence of SEQ ID NO: 28 or SEQ ID NO: 29 and that is conjugated to one poly (ethylene glycol) residue at the C-terminal lysine residue or a polypeptide obtained with the method as reported herein for use in the treatment or prevention of Alzheimer's disease.

Another aspect as reported herein is a method of treatment comprising administering to a subject in need thereof a therapeutically effective amount of a polypeptide that has the amino acid sequence of SEQ ID NO: 28 or SEQ ID NO: 29 and that is conjugated to one poly (ethylene glycol) residue at the C-terminal lysine residue or a polypeptide obtained with a method as reported herein.

Also an aspect as reported herein is a polypeptide that comprises the amino acid sequence of SEQ ID NO: 28 or SEQ ID NO: 29 and that is conjugated to one poly (ethylene glycol) residue at the C-terminal lysine residue.

A further aspect as reported herein is a pharmaceutical composition comprising a polypeptide that comprises the amino acid sequence of SEQ ID NO: 28 or SEQ ID NO: 29 and that is conjugated to one poly (ethylene glycol) residue at the C-terminal lysine residue. Another aspect as reported herein is a polypeptide that comprises the amino acid sequence of SEQ ID NO: 28 or SEQ ID NO: 29 and that is conjugated to one poly (ethylene glycol) residue at the C-terminal lysine residue for the treatment of a neurodegenerative disorder. In one embodiment the neurodegenerative disorder is Alzheimer's disease.

DETAILED DESCRIPTION OF THE INVENTION

Herein is reported a method for the selective C-terminal, covalent conjugation of a polypeptide to one (or more) poly (ethylene glycol) residue(s). This is a method, in which a small peptide covalently conjugated to a poly (ethylene glycol) residue is enzymatically transferred to a polypeptide to be PEGylated.

The enzymatic method as reported herein provides an alternative to the traditional chemical and special substrate requiring procedures. By applying the current method separation of isoforms is no longer necessary as only a single, site-specific modification is obtained. Additionally, the mild reaction conditions prevent protein denaturation and, thus, limit product loss. Furthermore, it is possible to site-specifically mono-PEGylate naturally occurring polypeptides making engineered mutants superfluous.

The term "amino acid" as used herein denotes the group of carboxy α-amino acids, which directly or in form of a precursor can be encoded by a nucleic acid. The individual amino acids are encoded by nucleic acids consisting of three nucleotides, so called codons or base-triplets. Each amino acid is encoded by at least one codon. This is known as "degeneration of the genetic code". The term "amino acid" as used within this application denotes the naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

Methods and techniques known to a person skilled in the art, which are useful for carrying out the current invention, are described e.g. in Ausubel, F. M. (ed.), Current Protocols in Molecular Biology, Volumes Ito III (1997), Wiley and Sons; Sambrook et al., Molecular Cloning: A Laboratory Manual, Second Edition, Cold Spring Harbor Laboratory Press, Cold Spring Harbor, N.Y. (1989).

As used herein, "pharmaceutically acceptable carrier" includes any and all solvents, dispersion media, coatings, antibacterial and antifungal agents, isotonic and absorption/resorption delaying agents, and the like that are physiologically compatible. In one embodiment the carrier is suitable for injection or infusion.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

The terms "poly (ethylene glycol) residue" or "PEG" or "PEG molecule" denote a molecule or residue containing poly (ethylene glycol) as main fraction or part. Such poly (ethylene glycol) may contain one or more further chemical group(s), which are necessary for binding reactions, which results from the chemical synthesis of the molecule, or which is a spacer for optimal distance of parts of the molecule. These further chemical groups are not used for the calculation of the molecular weight of the poly (ethylene glycol). In addition, such a poly (ethylene glycol) may comprise one or more poly (ethylene glycol)-chains, which are linked together. A poly (ethylene glycol) with more than one poly (ethylene glycol)-chain is called multiarmed or branched poly (ethylene glycol). Branched poly (ethylene glycol) can be prepared, for example, by the addition of polyethylene oxide to various polyols, including glycerol, pentaerythriol, and sorbitol. Branched poly (ethylene glycol) is reported in, for example, EP 0 473 084, and U.S. Pat. No. 5,932,462. In one embodiment the poly (ethylene glycol) residue is a poly (ethylene glycol) residue with a molecular weight of 20-35 kDa and is a linear poly (ethylene glycol) residue. In another embodiment the poly (ethylene glycol) residue is a poly (ethylene glycol) residue with a molecular weight of more than 35 kDa, especially with 40 kDa, and is a branched poly (ethylene glycol) residue. In a further embodiment the poly (ethylene glycol) residue has a weight of 40 kDa and is a two-armed poly (ethylene glycol) residue.

The term "PEGylation" denotes the covalent linking of a poly (ethylene glycol) molecule at the N-terminus of a polypeptide and/or at an internal lysine residue. PEGylation of polypeptides is widely known in the state of the art and reviewed by, for example, Veronese, F. M., Biomaterials 22 (2001) 405-417. A PEG molecule can be linked to a polypeptide using different functional groups and poly (ethylene glycol) molecules with different molecular weight, linear and branched PEG as well as different linking groups (see also Francis, G. E., et al., Int. J. Hematol. 68 (1998) 1-18; Delgado, C., et al., Crit. Rev. Ther. Drug Carrier Systems 9 (1992) 249-304). PEGylation of polypeptides can be performed in aqueous solution with PEGylation reagents as described, for example, in WO 00/44785, in one embodiment using NHS-activated linear or branched PEG molecules of a molecular weight between 5 kDa and 40 kDa. PEGylation can also be performed at the solid phase according to Lu, Y., et al., Reactive Polymers 22 (1994) 221-229. Not randomly, N-terminally PEGylated polypeptides can also be produced according to WO 94/01451.

A "polypeptide" is a polymer consisting of amino acid residues covalently joined by peptide bonds, whether produced naturally or synthetically. Polypeptides of less than about 20 amino acid residues may be referred to as "peptides", whereas molecules consisting of two or more polypeptides or comprising one polypeptide with a length of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

Hoess et al. created the trypsin mutant D189K, K60E, N143H, E151H (trypsin-4x-mutant), which is capable to overcome the predominant affinity of trypsin to hydrolysis. In addition this mutant does not show significant proteolysis C-terminal of lysine and arginine. The trypsin-4x-mutant recognizes a specific motif, the sequence tyrosine-arginine-histidine (YRH). The trypsin-4x-mutant can specifically interact with this recognition site by building chelate complexes involving $Zn^2$ ions between the histidine residues. This recognition sequence has a very small likelihood to appear in human polypeptides. Thus, multiple site-specific modifications and/or undesired cleavage are rather unlikely. Further modification of this sequence to ensure best recognition by the trypsin-4x-mutant led to the development of a specific tag, a modified "trypsin site" consisting of the amino acid sequence tyrosine-arginine-histidine-alanine-alanine-glycine (YRHAAG) (SEQ ID NO: 01). This peptide can be fused to a polypeptide's C-terminus, hence building the substrate for the trypsin-4x-mutant. In addition, a target peptide is necessary to make site-specific PEGylation possible. This peptide should overlap with the "trypsin site", and consist of the amino acid sequence arginine-histidine-alanine-lysine (RHAK) (SEQ ID NO: 02). This target peptide can be enzymatically transferred to a diversity of molecules. The trypsin-4x-mutant cleaves the peptide bond between the tyrosine and histidine residues, thereby displacing part of the "trypsin site" (RHAAG) (SEQ ID NO: 03). A short non-native amino acid sequence (YRHAK) (SEQ ID NO: 04) remains between the protein and the attached nucleophile. However, this short elongation is fairly shielded by the attached nucleophile, e.g. a poly (ethylene glycol) residue, and, thus, immunogenic activity of this peptide is rather unlikely.

The modifications in the trypsin-4x-mutant are not capable of absolutely eliminating the hydrolytic side reaction. Thus, a maximum yield can only be achieved when the reaction is stopped as in one embodiment of the methods as reported herein at the correct time by addition of ethylenediaminetetraaceticacid acid (EDTA) to complex $Zn^{2+}$ ions or by adjusting the pH to an acidic level as in another embodiment of the methods as reported herein, leaving the pH range necessary for proper enzyme functionality.

Some recombinant proteins contain special fusion tags, e.g. to ease subsequent purification steps or to simply allow expression of constructs otherwise too small to ensure proper production in the host cell. Some well established tags are the hexahistidine-tag (His-tag) or the Strep-tag. His-tags can be used to purify fused proteins through metal-affinity chromatography while a Strep-tag is applied for purification of fusion proteins using streptavidin columns (Terpe, K., Appl. Microbiol. Biotechnol. 60 (2003) 523-533). Under some circumstances it is necessary to cleave these tags, e.g. for pharmaceuticals or to simply ensure proper refolding, if necessary. Enzymatic cleavage using proteases with defined recognition sites is the most desirable approach. Immunoglobulin A protease (IgA protease) derived from *Neisseria gonorrhoeae* is used in one embodiment of the methods as reported herein. The recognition site of the IgA Protease is reported as Yaa Pro↓Xaa Pro (Yaa stands for Pro or rarely for Pro in combination with Ala, Gly or Thr: Pro Ala, Pro Gly, or Pro Thr; Xaa stands for Thr, Ser or Ala). Synthetic peptide substrates for the IgA protease from *Neisseria gonorrhoeae* are the autoproteolytic sites known (see e.g. Wood and Burton, Infection and Immunity 59 (1991) 1818-1822). The recognition sites known for IgA proteases comprise the following sequences with "↓" denoting the position of the cleaved bond:

Pro-Ala-Pro ↓ Ser-Pro,   (SEQ ID NO: 05)

Pro-Pro ↓ Ser-Pro,   (SEQ ID NO: 06)

Pro-Pro ↓ Ala-Pro,   (SEQ ID NO: 07)

Pro-Pro ↓ Thr-Pro,   (SEQ ID NO: 08)

```
Pro-Pro ↓ Gly-Pro,                                      (SEQ ID NO: 09)

Ala-Pro ↓ Arg-Pro,                                      (SEQ ID NO: 14)

Pro-Ala-Pro ↓ Arg-Pro,                                  (SEQ ID NO: 15)

Pro-Ala-Pro ↓ Gly-Pro,                                  (SEQ ID NO: 16)

Pro-Pro-Thr-Pro ↓ Ser-Pro,                              (SEQ ID NO: 17)

Pro-Arg-Pro-Pro ↓ Thr-Pro,                              (SEQ ID NO: 18)

Pro-Arg-Pro-Pro ↓ Ser-Pro,                              (SEQ ID NO: 19)

Pro-Arg-Pro-Pro ↓ Ala-Pro,                              (SEQ ID NO: 20)

Pro-Arg-Pro-Pro ↓ Gly-Pro,                              (SEQ ID NO: 21)

Lys-Pro-Ala-Pro ↓ Ser-Pro,                              (SEQ ID NO: 22)

Ser-Thr-Pro-Pro ↓ Thr-Pro,                              (SEQ ID NO: 23)

Val-Ala-Pro-Pro ↓ Ser-Pro,                              (SEQ ID NO: 24)

Ala-Pro-Arg-Pro-Pro ↓ Gly-Pro,                          (SEQ ID NO: 25)

Pro-Ala-Pro-Arg-Pro-Pro ↓ Gly-Pro,                      (SEQ ID NO: 26)
``` wherein the first three are more frequently chosen.

Thus, in one embodiment the fusion polypeptide comprises in N- to C-terminal direction a His-tag, a spacer, an IgA protease cleavage site (IgA-site), a polypeptide of interest, a trypsin-4x-mutant cleavage site (tryp-site), and optionally a streptavidin-tag (strep-tag).

The enzymatic technique of site-specific modification using the trypsin-4x-mutant made it necessary to create special constructs carrying appendages essential for this type of modification.

Thus, in one embodiment of the methods as reported herein the fusion polypeptide comprises in N- to C-terminal direction the polypeptide to be PEGylated, a trypsin-4x-mutant cleavage site and a Strep-tag. In another embodiment the nucleic acid encoding the fusion polypeptide comprising in 5' to 3' direction i) a nucleic acid encoding the polypeptide to be PEGylated, ii) a nucleic acid encoding an amino acid sequence of SEQ ID NO: 01, and iii) a nucleic acid encoding a Strep-tag of SEQ ID NO: 13 or 27.

Therefore, one aspect as reported herein is a method for producing a polypeptide conjugated to a poly (ethylene glycol) residue comprising the step of a) incubating a fusion polypeptide, which is encoded by a nucleic acid comprising in 5' to 3' direction i) a nucleic acid encoding the polypeptide, and ii) a nucleic acid encoding an amino acid sequence of SEQ ID NO: 01, and a target polypeptide, which has the amino acid sequence of SEQ ID NO: 02 and which is covalently conjugated to a poly (ethylene glycol) residue at the C-terminal lysine residue, with the trypsin mutant D189K, K60E, N143H, E151H, and b) recovering and thereby producing the polypeptide conjugated to one poly (ethylene glycol) residue from the incubation mixture.

In one embodiment the fusion polypeptide is encoded by a nucleic acid comprising in 5' to 3' direction i) a nucleic acid encoding the polypeptide to be PEGylated, ii) a nucleic acid encoding an amino acid sequence of SEQ ID NO: 01, and iii) a nucleic acid encoding an amino acid sequence of SEQ ID NO: 13 or 27.

In one embodiment the method comprises as first step:
a-1) cultivating a cell comprising a nucleic acid encoding a fusion polypeptide comprising in 5' to 3' direction
   i) a nucleic acid encoding a polypeptide to be PEGylated,
   ii) a nucleic acid encoding an amino acid sequence of SEQ ID NO: 01, and
   iii) a nucleic acid encoding an amino acid sequence of SEQ ID NO: 13 or 27 and recovering the fusion polypeptide from the cell and/or the cultivation medium.

In one embodiment the incubating comprises
   i) incubating the fusion polypeptide and the target peptide with guanidinium hydrochloride in a buffered solution,
   ii) incubating the trypsin mutant D189K, K60E, N143H, E151H with a Zn(II)-salt,
   iii) combining and incubating the incubation mixtures of i) and ii).

The current invention is exemplified in the following by using the IGF-I protein, which was available in sufficient quantities in our laboratory at the time the invention was made. This shall not be construed as a limitation, it is provided merely as an example, as the current invention may be practiced with almost any polypeptide. The true scope of the invention is set forth in the appended claims.

Exemplary constructs carried a His-tag, a spacer and an IgA protease cleavage site (IgA-site) N-terminal of the IGF-I polypeptide (part) and the trypsin cleavage site (tryp-site) and optionally a streptavidin-tag (strep-tag) C-terminal of the IGF-I-polypeptide (part) (see also FIG. 1):

```
                                                                          (SEQ ID NO: 10)
            His-tag - spacer - IgA-site - wt-hIGF - tryp-site - strep-tag (SEQ ID NO: 11)
            His-tag - spacer - IgA-site - wt-hIGF - tryp-site (SEQ ID NO: 12)
            His-tag - spacer - IgA-site - hIGF (K27R, K65R) - tryp-site
```

Experiments to determine the kinetics of the transesterification reaction catalyzed by the trypsin-4x-mutant can be carried out in a final volume of as less as 400 μl.

The IGF-I comprising fusion polypeptide to be site-specifically modified can be incubated with 2 M tris (hydroxymethane) aminomethane (TRIS) buffer (final concentration of 0.2 M), pH 8.0, the nucleophile (RHAK-6CF (SEQ ID NO: 02) or RHAK-MCa-PEG20000 (SEQ ID NO:

02)), and guanidinium hydrochloride (Gdm-HCl) prior to the enzymatic reaction. Without being bound by theory, in this way the solubility of the IGF construct could be maintained and the small concentration of guanidinium hydrochloride probably induced a partial denaturation and, thus, provided for a better accessibility of the C-terminus with "trypsin site" during the enzymatic reaction. The trypsin-4×-mutant can be preincubated in the presence of $Zn^{2+}$ ions. Good enzymatic activity can be achieved by combining the two reaction mixtures A and B with mixture A comprising the IGF-I comprising fusion polypeptide and mixture B comprising the trypsin-4×-mutant. The reaction mixtures can have a pH value of pH 8.0. The total reaction mixture can be incubated at 30° C. while gently shaking A total reaction time of 180 min. can be applied and samples may be taken every 30 min. The enzymatic reaction can be stopped by complexing the $Zn^{2+}$ ions with EDTA. Finally, the volume can be adjusted by adding a buffer solution (buffer S comprising 100 mM TRIS, 150 mM NaCl, pH 8.0), to a final dilution factor of 1:2. The samples can be analyzed by SEC. Depending on which label was used, different SEC columns can be applied. For example, for RHAK-6CF a Superdex™ Peptide column with a separation range of 100-7000 Da can be used, for RHAK-MCa-PEG20000 a Superdex™ 75 column with a separation range of 3000-70000 Da can be used (GE Healthcare).

The yield for site-specific modification with RHAK-6CF can be determined as follows. A concentration dilution series of free RHAK-6CF can be prepared (0.5, 1, 5, 10, 25, 50 and 100 µg/ml). Buffer S can be used as a solvent, as RHAK-6CF fluorescence is pH sensitive. Calibration samples can be analyzed by SEC. The peak areas of RHAK-6CF comprising peaks resulting of radiation emission at 514 nm can be determined for the different concentrations and plotted, thus, providing a calibration curve. Reaction samples can be analyzed by SEC in the same way as the calibration samples and the peak area of the fluorescent product can be determined. The amount of formed RHAK-6CF and hence, the yield of site-specific modification with this nucleophile can be determined by using the calibration curve.

For all constructs the yield increased with time. After approximately 150 min. a maximum yield can be obtained. The construct wt-hIGF-trypsin site-strep tag provided for the best results with a yield of 17.5% after 150 min. In contrast, wt-hIGF-trypsin site and mut-hIGF (K27R, K65R) provided for smaller and relatively equal maximal outcomes of 11.9% after 150 min. and 13.0% after 180 min., respectively. The increase in yield with time during site-specific modification with RHAK-6CF is shown in FIG. 2 B.

When RHAK-MCa-PEG20000 was used as a nucleophile, problems in separation of free, unconjugated RHAK-MCa-PEG20000 and RHAK-MCa-PEG20000-labeled IGF-I have occurred. This may be due to the similar size of nucleophile and the conjugation product. Thus, it was not possible to determine the yield for site-specific modification through the increase in product in this case and a different approach was necessary. Because only a single site-specific modification would occur, the decrease in unmodified IGF-I (educt) may be equivalent to an increase in conjugation product. The decrease in unmodified IGF-I was estimated through the HPLC chromatogram peak area resulting from the absorbance at 226 nm. As for modification with RHAK-6CF, the yield for modification with RHAK-MCa-PEG20000 increased with time (FIGS. 3 and 4). With the construct wt-hIGF-tryp site-strep tag surprisingly the highest yield after 180 min. with 23.1% could be obtained. Almost equal results were obtained for mut-IGF (K27R, K65R)-tryp site (20.6% after 180 min.) and wt-hIGF-tryp site (19.9% after 180 min.).

TABLE 1

Comparison of yield in site-specific modification with RHAK-6CF or RHAK-MCa-PEG20000

| IGF-I construct | nucleophile | maximum yield [%] | incubation time required for maximum yield [min] |
|---|---|---|---|
| wt-hIGF-tryp site-strep tag | RHAK-6CF | 17.5 | 150 |
| | RHAK-MCa-PEG20000 | 23.1 | 180 |
| wt-hIGF-tryp site | RHAK-6CF | 11.9 | 150 |
| | RHAK-MCa-PEG20000 | 19.9 | 180 |
| mut-hIGF-tryp site | RHAK-6CF | 13.0 | 180 |
| | RHAK-MCa-PEG20000 | 20.6 | 180 |

A comparison of site-specific modification with either RHAK-6CF or RHAK-MCa-PEG20000 of different fusion polypeptides is shown in Table 1. In general, modification with RHAK-MCa-PEG20000 had a yield higher than modification with RHAK-6CF. But also the polypeptide to be PEGylated had an influence on the yield. With the construct wt-hIGF-tryp site-strep tag the highest yield can be obtained independently of the target polypeptide (or nucleophile). The constructs wt-hIGF-tryp site and mut-hIGF-tryp site delivered almost equal results. Thus, it has been found that the presence of a Strep Tag enhances C-terminal site-specific enzymatic modification.

To verify the mono- and C-terminal site-specific modification, the labeled IGF-I constructs can be analyzed by mass spectrometry. For this purpose a 400 µl reaction for the site-specific modification with RHAK-6CF of each construct can be used. The reaction can be incubated for 150 min. at 30° C. and subsequently stopped by the addition of 200 µl of a 10 mM EDTA solution. The reaction solution can thereafter be diluted to 1:2 by adding 200 µl of buffer S. Whole labeling reactions can be purified by size exclusion chromatography. RHAK-6CF comprising IGF-I fusion polypeptide can be collected and concentrated. The purified site-specifically modified IGF-I constructs can subsequently be analyzed by mass spectrometry techniques for total molecular weight. The molecular weight of fragments resulting from a digest (Asp-N-digest) verified the single, C-terminal site-specific modification with RHAK-6CF for all constructs.

Thus, a new enzymatic method for C-terminal site-specific modification using the trypsin-4× mutant to modify an engineered polypeptide, e.g. IGF-I, carrying a "trypsin site" has been found. Using this new technique, it was possible to site-specifically modify the polypeptide, e.g. wild type human IGF-I, without at risk to obtain heterogeneous, activity-decreasing modification. These unwanted side products often limited PEGylation applications in the past. This new enzymatic approach can readily be used in the preparation of PEGylated proteinaceous pharmaceuticals. Instead of PEG comprising target polypeptides, other potential nucleophiles can be used, such as target polypeptides comprising/conjugated to fluorescent dyes, biotin, saccharides and others. The simple addition of the short peptide RHAK (SEQ ID NO: 02) can make these usable for transfer with the trypsin-4×-mutant system.

The reaction conditions for the enzymatic PEGylation of the wt-hIGF-tryp site-strep tag construct were further optimized by reducing the amount of label (RHAK-MCa- PEG20000) and the amount of trypsin-4×-mutant as well as by replacing the TRIS buffer with a HEPES buffer.

The following examples, sequence listing and figures are provided to aid the understanding of the present invention, the true scope of which is set forth in the appended claims. It is understood that modifications can be made in the procedures set forth without departing from the spirit of the invention.

DESCRIPTION OF THE SEQUENCE LISTING

SEQ ID NO: 01 Modified trypsin site (tryp-site).
SEQ ID NO: 02 Target peptide required for site-specific PEGylation.
SEQ ID NO: 03 Displacing part of the trypsin site.
SEQ ID NO: 04 Remaining peptide sequence.
SEQ ID NO: 05 to 09 and 14 to 26 IgA-protease cleavage site
SEQ ID NO: 10 His-tag-spacer-IgA-site-wt-hIGF-tryp-site-strep-tag.
SEQ ID NO: 11 His-tag-spacer-IgA-site-wt-hIGF-tryp-site.
SEQ ID NO: 12 His-tag-spacer-IgA-site-hIGF (K27R, K65R)-tryp-site.
SEQ ID NO: 13 and 27 Strep-tag.
SEQ ID NO: 28 Amino acid sequence of mono-PEGylated human IGF-I comprising an N-terminal his-tag and an IgA protease cleavage site.
SEQ ID NO: 29 Amino acid sequence of mono-PEGylated human IGF-I.

DESCRIPTION OF THE FIGURES

FIG. 1 Schematic depiction of different constructs.

ABBREVIATIONS

Figure 2:
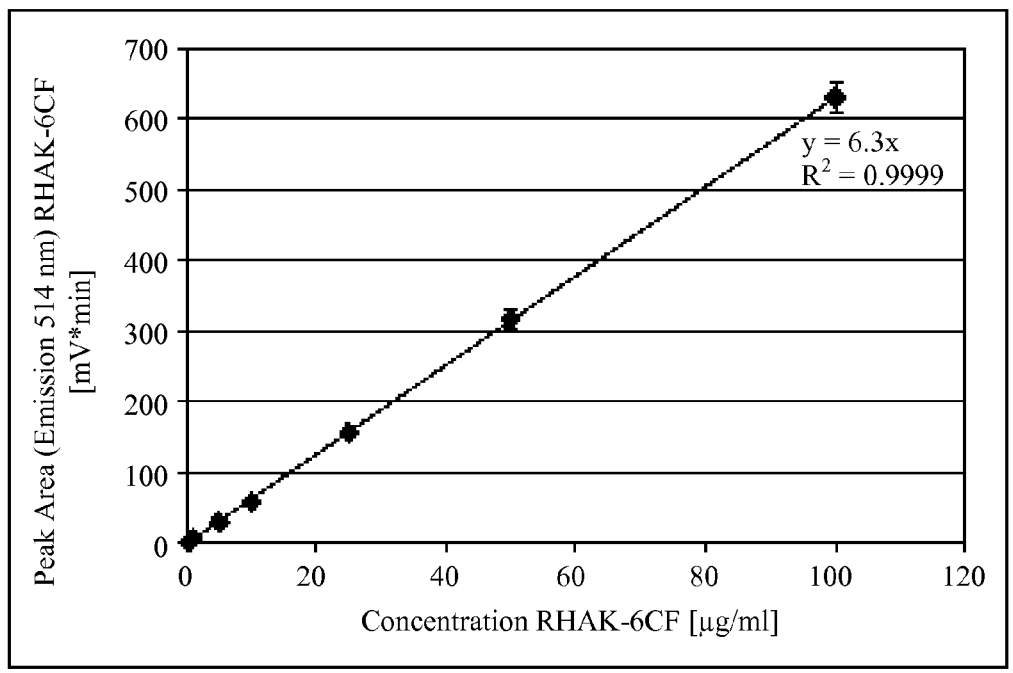
FIG. 2A A dilution series with the following concentrations prepared in 100 mM tris, 150 mM NaCl, pH 8.0 was analyzed using SEC: 0.5, 1, 5, 10, 25, 50, 100 µg/ml. The peak area of the RHAK-6CF emission at 514 nm was determined and plotted in relevance to the concentration. The coefficient of determination ($R^2$) and the equation for the applied trend line are shown. Each data point is the result of 3 repetitive experiments and shown ±standard error. This calibration curve for RHAK-6CF.
FIG. 2B Labeling reactions were prepared according to 4.3.8 for RHAK-6CF labeling. Samples were analyzed by SEC. (left): wt-hIGF—tryp site-strep tag, (middle): wt-hIGF—tryp site, (right): mut-hIGF (K27R, K65R)—tryp site. This is a yield of RHAK-6CF labeling.
Figure 2:
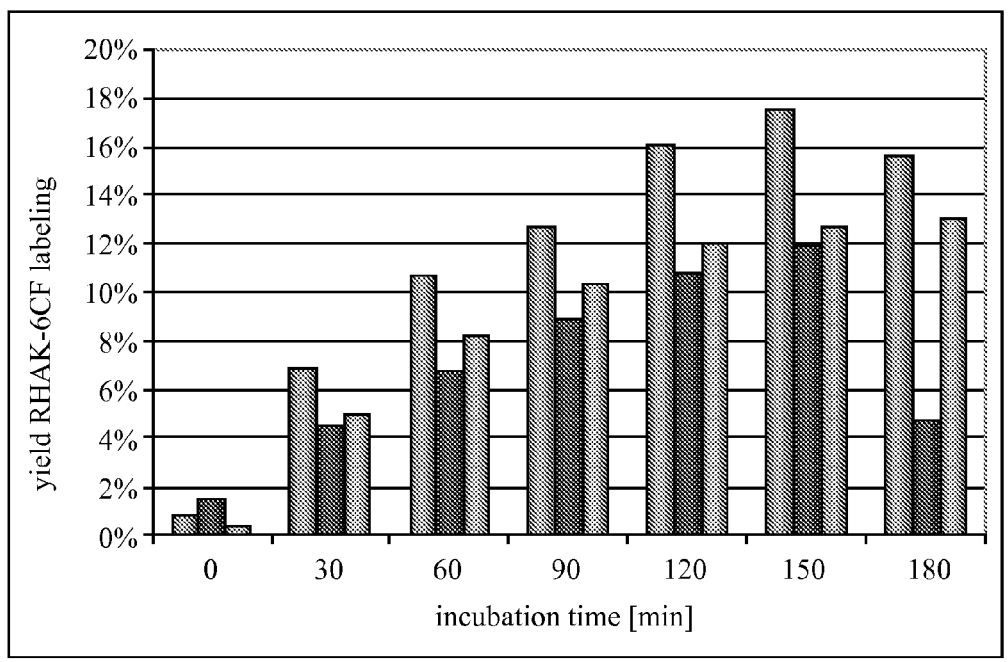
Figure 3:
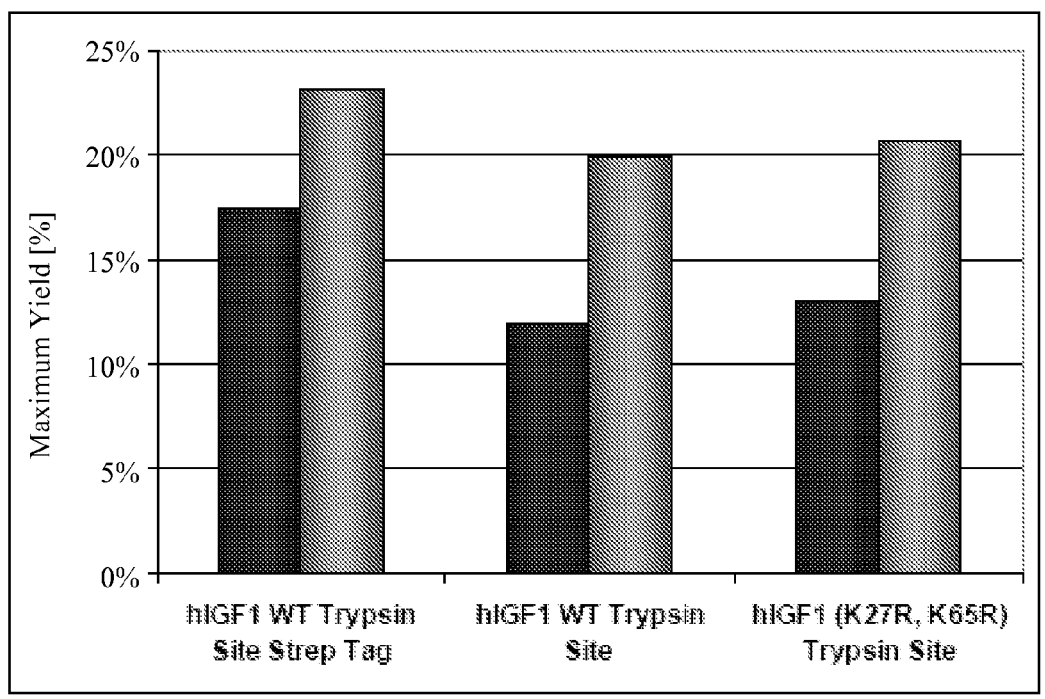
FIG. 3 Comparison of yield in site-specific modification with RHAK-6CF or RHAK-MCa-PEG20000. (left): RHAK-6CF, (right): RHAK-MCa-PEG20000.

"trypsin side" amino acid sequence YRHAAG
6-CF carboxy fluorescein
Gdm-HC1 guanidinium hydrochloride
His-tag poly histidine tag
MCa methyl coumarin
PEG poly (ethylene glycol)
Strep streptavidin
TRIS 2-amino-1-hydroxymethyl-1,3-propane diol
Tryp "trypsin site"
IGF-I insulin like growth factor 1 trypsin-4×-mutant mutant trypsin D189K, K60E, N143H, E151H

Materials and Methods:
Analytic Size Exclusion Chromatography
Buffer: 0.5 M TRIS, 0.15 M NaCl, pH 7.5
Column: Superdex™ Peptide 10/300 GL
System: Dionex
Method: Isocratic elution was carried out with a flow of 0.5 ml/min. The total cycle time was 70 min. 50 µl of sample was injected. The course of separation was tracked by following the absorbance signals at 220 and 280 nm.
Size Exclusion Chromatography During Labeling
Buffer: 100 mM TRIS, 150 mM NaCl, pH 8.0
Column: Superdex™ Peptide 10/300 GL (RHAK-6CF Labeling) Superdex™ 75 10/300 GL (RHAK-MCa-PEG20000 labeling)
System: Gynkotek (RHAK-6CF labeling) Dionex (RHAK-MCa-PEG20000 labeling, see Table 8)
RHAK-6CF labeling method: Isocratic elution was carried out with a flow of 0.5 ml/min. The total cycle time was 60 min.
RHAK-MCa-PEG20000 labeling method: Isocratic elution was carried out with a flow of 0.75 ml/min.
The total cycle time was 45 min.
50 µl of sample (250 µl for preparative issues) were injected. The course of separation was tracked by following the absorbance signals at 220 nm, 280 nm, 320 nm (RHAK-MCa-PEG20000 labeling) and the fluorescence signal (extinction=490 nm, emission=514 nm) (RHAK-6CF labeling).

EXAMPLE 1

Site Specific Modification
Site-specific labeling of IGF-I constructs was accomplished with RHAK-6CF and RHAK-MCa-PEG20000.

TABLE 2

Components for site-specific modification. Concentrations and specifications are given for stock solutions.

| component | concentration stock solution | in |
|---|---|---|
| wt-hIGF - tryp site - strep tag | 2 mg/ml | in 10 mM sodium acetate buffer, pH 4.5 |
| wt-hIGF - tryp site | 2 mg/ml | in 10 mM sodium acetate buffer, pH 4.5 |
| mut-hIGF (K27R, K65R) - tryp site | 2 mg/ml | in 10 mM sodium acetate buffer, pH 4.5 |
| trypsin 4x mutant | 200 µM | in 1 mM HCl |
| TRIS | 2M | in $H_2O$, pH 8.0 |
| buffer S (Tris, NaCl) | 100 mM, 150 mM | in $H_2O$, pH 8.0 |
| RHAK-MCa-PEG20000 | 200 mg/ml | in $H_2O$ |
| RHAK-6CF | 10 mg/ml | in $H_2O$ |
| Gdm-HCl | 4M | in $H_2O$ |
| $ZnCl_2$ | 20 mM | in $H_2O$ |

TABLE 3

Controls performed for site-specific modifications reactions. Controls # 1, # 3a, # 3b were performed for each hIGF-I construct.

| control | hIGF-I construct | trypsin 4x mutant | RHAK-6CF | RHAK MCa-PEG20000 |
|---|---|---|---|---|
| # 1 | + | + | − | − |
| # 2a | − | − | + | − |
| # 2b | − | − | − | + |

TABLE 3-continued

Controls performed for site-specific modifications reactions.
Controls # 1, # 3a, # 3b were performed
for each hIGF-I construct.

| control | hIGF-I construct | trypsin 4x mutant | RHAK-6CF | RHAK MCa-PEG20000 |
|---|---|---|---|---|
| # 3a | + | + | + | − |
| # 3b | + | + | − | + |

Each construct was labeled with either RHAK-6CF or RHAK-MCa-PEG20000. In addition controls according to Table 2 were performed.

The concentrations of the different compounds in the final labeling reactions are listed in Table 4. All reactions were performed in 650 µl siliconized tubes. The proteins were diluted in 2 M TRIS buffer. Subsequently the labeled peptide and guanidinium hydrochloride were added. This mixture (A) was incubated at 30° C. for 10 min. Mixture B consisting of trypsin 4× mutant, $ZnCl_2$ and buffer S (100 mM TRIS, 150 mM NaCl, pH 8.0) was incubated at the same conditions as mixture A. The necessary volume of buffer S was chosen to provide for a total reaction volume of 400 µl for labeling reactions and 250 µl for controls. Mixtures A and B were combined and incubated at 30° C. while gently shaking.

To stop the enzymatic reaction the reaction mixture was combined with half of its volume with 10 mM EDTA (prepared in buffer S) and the same volume of buffer S for a dilution factor of 1:2. A total reaction time of 180 min was applied.

TABLE 4

Concentrations of all compounds for site-specific modification in reactions. A reaction volume of 400 µl for labeling reactions and 250 µl for controls was applied. Reactions were performed using either RHAK-6CF or RHAK-MCa-PEG20000 as a label.

| Mixture | Component | wt-hIGF-I trypsin Site strep Tag | | wt-hIGF-I trypsin Site | | mut-hIGF-I (K27R, K65R) trypsin Site | |
|---|---|---|---|---|---|---|---|
| A | Protein | 1 mg/ml | 107.1 µM | 1 mg/ml | 120.6 µM | 1 mg/ml | 119.7 µM |
|   | RHAK-6CF | 1.17 mg/ml | 1071 µM | 1.32 mg/ml | 1206 µM | 1.31 mg/ml | 1197 µM |
|   | RHAK-MCa-PEG20000 | 24.6 mg/ml | 1071 µM | 27.7 mg/ml | 1206 µM | 27.5 mg/ml | 1197 µM |
|   | TRIS | | 200 mM | | 200 mM | | 200 mM |
|   | Gdm HCl | | 200 mM | | 200 mM | | 200 mM |
| B | Trypsin 4x Mutant | | 20 µM | | 20 µM | | 20 µM |
|   | $ZnCl_2$ | | 100 µM | | 100 µM | | 100 µM |
|   | buffer S (Tris, NaCl) | add to final volume | | add to final volume | | add to final volume | |

EXAMPLE 2

Optimization of Site Specific Modification

Figure 4:
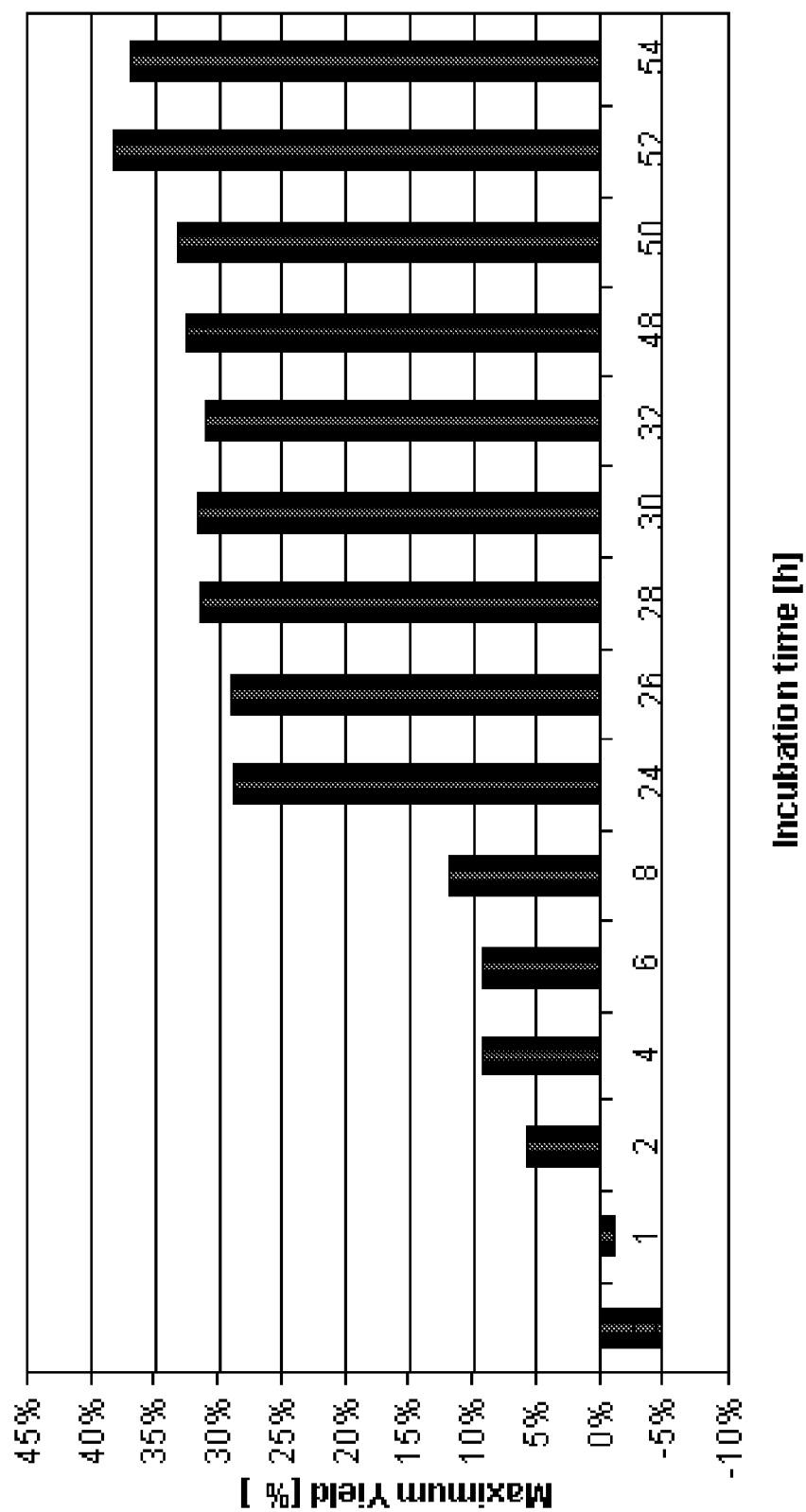
FIG. 4 Time-dependent increase of C-terminally modified IGF-I under optimized conditions (nucleophile: RHAK-MCa-PEG20000).

The reaction was carried out in a volume of 1000 µA at room temperature. The trypsin-4×-mutant was preincubated in the presence of $ZnCl_2$ and the PEG label for 10 min. at 30° C. Afterwards guanidinium HCl and wt-hIGF-tryp site-strep site was added to achieve the final concentrations given below. The reaction mixture was incubated for up to 54 hours at 20° C. A product yield of >25% was achieved after 24 h reaching a maximum of 32.6% after 52 hours (see FIG. 4).

Reaction Conditions:
100 µM wt hIGF-I Trypsin Site Strep Tag
2 µM Trypsin 4× mutant
500 µM RHAK-MCa-PEG20000
10 µM $ZnCl_2$
100 mM HEPES
150 mM NaCl
1 mM $CaCl_2$
200 mM Gdm HCl

EXAMPLE 3

In Vitro IGF-IR Phosphorylation by Recombinant Wt and Mutant IGF-I Variants and Mono-PEGylated IGF-I A phospho-IGF-IR specific ELISA was used to quantify activation of IGF-IR by the different IGF-I variants. After serum starvation over night, recombinant NIH-3T3 cells expressing human IGF-IR were incubated with different concentrations of IGF-I variants in order to allow for binding and activation of the IGF-IR in a cellular context. Following stimulation, cells were subjected to lysis using cold lysis buffer (25 mM MES, pH 6.5, 150 mM NaCl, 2% Triton-X100, 60 mM β-octylglycosid, 2 mM $Na_3VO_4$, Complete™ protease inhibitor) in order to preserve the phosphorylation status. A biotinylated monoclonal antibody against the human IGF-IR alpha chain (MAK<hu IGF-IRα>hu-la-IgG-Bi, Roche Diagnostics GmbH) was used to capture total IGF-IR to the surface of a streptavidin coated microplate, and a monoclonal antibody against phosphorylated Tyr1135/1136 within the IGF-IR kinase domain (Cell Signaling #3024L) was used to determine the fraction of activated IGF-IR. Cells stimulated with 10 nM human IGF-I were used as max control, cells without stimulation as min control. Percent activation of the IGF-IR was calculated as (result-min)/(max-min). $IC_{50}/EC_{50}$-values were determined by curve fitting using GraphPad Prism 4.0 software.

TABLE 5

Activation of IGF-1R by the different IGF-I variants.

| Sample | $EC_{50}$ [nM] |
|---|---|
| rhIGF-I (K27R, K65R) | 1.2 |
| monoPEGylated rhIGF-I (K27R, K65R) | 8.1 |
| wt-rhIGF-I | 1.0 |
| wt-rhIGF-trypsin site-Strep-Tag | 1.7 |
| wt-rhIGF-I-YRHAK MCa PEG20000 | 18.4 |
| RHAK-MCa-PEG20000 | not determinable |

The invention claimed is:

1. A polypeptide consisting of the amino acid sequence of SEQ ID NO: 28 that is conjugated to poly (ethylene glycol) at the C-terminal lysine residue of the polypeptide.

2. A pharmaceutical composition comprising the polypeptide according to claim 1.

3. A polypeptide consisting of the amino acid sequence of SEQ ID NO: 29 that is conjugated to poly (ethylene glycol) at the C-terminal lysine residue of the polypeptide.

* * * * *